United States Patent [19]

Fischell

[11] 4,096,866

[45] Jun. 27, 1978

[54] RECHARGEABLE BODY TISSUE STIMULATOR WITH BACK-UP BATTERY AND PULSE GENERATOR

[75] Inventor: Robert E. Fischell, Silver Spring, Md.

[73] Assignee: The Johns Hopkins University, Baltimore, Md.

[21] Appl. No.: 820,545

[22] Filed: Jul. 29, 1977

Related U.S. Application Data

[62] Division of Ser. No. 682,505, Apr. 30, 1976, abandoned.

[51] Int. Cl.² .............................................. A61N 1/36
[52] U.S. Cl. ......................... 128/419 PG; 128/419 PS
[58] Field of Search ....... 128/419 P, 419 PG, 419 PS, 128/419 PT, 420 R, 421, 422, 423

[56] References Cited

U.S. PATENT DOCUMENTS

| | | | |
|---|---|---|---|
| 3,454,012 | 7/1969 | Raddi | 128/419 PG |
| 3,518,997 | 7/1970 | Sessions | 128/419 PG |
| 3,523,539 | 8/1970 | Lavezzo et al | 128/419 PG |
| 3,822,707 | 7/1974 | Adducci et al. | 128/419 PS X |
| 3,866,614 | 2/1975 | Svensson | 128/419 PG |
| 3,881,493 | 5/1975 | Cannon | 128/419 PG |

FOREIGN PATENT DOCUMENTS

| | | | |
|---|---|---|---|
| 1,082,752 | 9/1967 | United Kingdom | 128/419 P |
| 1,425,107 | 2/1976 | United Kingdom | 128/419 PS |

*Primary Examiner*—William E. Kamm
*Attorney, Agent, or Firm*—Robert E. Archibald

[57] ABSTRACT

An implanted tissue stimulator apparatus includes circuitry, powered by an implanted rechargeable battery, to produce electrical stimulation and apply it to selected body tissue. The condition of the rechargeable battery is monitored continuously and if the cell fails or its voltage drops below a preselected level, the stimulator reverts to a stand-by power source provided by a battery having an extremely long shelf-life. A back-up pulse generator is also provided and the control logic circuitry within the implanted stimulator monitors the operation of the pulse generator, in addition to the condition of the rechargeable battery, and if faulty operation of the pulse generator is detected the logic circuitry automatically switches to the back-up pulse generator in order to maintain adequate tissue stimulation.

8 Claims, 3 Drawing Figures

4,096,866

RECHARGEABLE BODY TISSUE STIMULATOR WITH BACK-UP BATTERY AND PULSE GENERATOR

RELATED APPLICATIONS

This application is a division of application Ser. No. 682,505, filed Apr. 30, 1976 which is now abandoned.

BACKGROUND OF THE INVENTION

The use of artificial electrical stimulation of human biological systems has been practiced for some time now, with the most well-known use being the implanted cardiac stimulators or pacers which generate and apply electrical stimulation pulses to the patient's heart at either a fixed rate or on demand. Electrical stimulation has also previously been proposed for the treatment of other physiological disorders such as, for example, epilepsy, cerebral palsy, dystonia, stroke and spasticity; as well as for aiding the breathing function by stimulation of the phrenic nerve, bladder stimulation to relieve urinary incontinency and to provide the voiding function as required, or stimulation of a particular muscle to make it function. In addition, it has been proposed that electrical stimulation of the striate cortex could be useful to provide visual sensations to patients who have lost the use of their eyes.

In the area of cardiac pacers particularly, it has been demonstrated that the acceptability and functioning of such pacer units could be improved significantly, from the standpoint of both physician and patient, by prolonging the useful life of the device; e.g., employing a rechargeable battery such as a single nickel-cadmium cell to power the pulse generating circuitry of the pacer unit and thereby reduce or completely obviate the necessity of having to replace depleted batteries, such as occurs when non-rechargeable type batteries are employed.

It is proposed in accordance with the present invention that the rechargeable battery be combined with a second battery purposely selected, in accordance with this invention, to have a very long shelf-life so as to be available as a stand-by power source if the rechargeable cell becomes unable to satisfactorily power the implanted stimulator circuitry. In addition to the redundant power source, a stand-by pulse generator is also contemplated, along with implanted logic circuitry which automatically switches to the stand-by power and stand-by pulse generator, as necessary to best insure prolonged fail-safe operation of the implanted tissue stimulator.

One object of the present invention is to provide an implantable tissue stimulator powered by a rechargeable battery and a back-up power source comprising a long shelf life power source, e.g., battery.

Another object of the present invention is to provide an implantable tissue stimulator which includes, in addition to pulse generating circuitry powered by a rechargeable battery, a stand-by power cell and a stand-by pulse generator which are automatically rendered effective by implanted logic circuitry, in the event of improper operation by the rechargeable battery and/or the normal pulse generator.

Other objects, purposes and characteristic features of the present invention will in part be pointed out as the description progresses and in part be obvious from the accompanying drawings, wherein:

IN THE DRAWINGS

Figure 1:
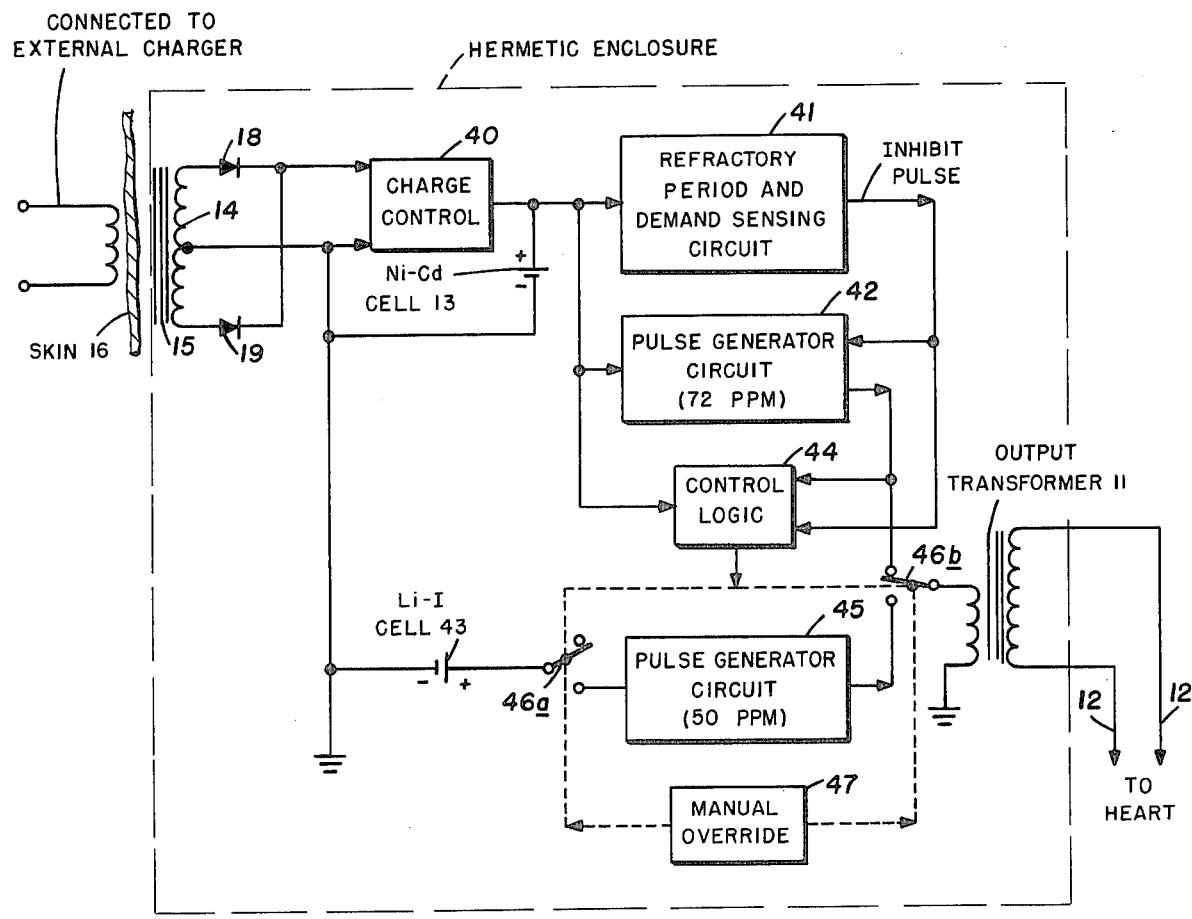
FIG. 1 is a block diagram illustrating a further embodiment of the present invention wherein stand-by or redundant power source and pulse generator are provided, along with suitable logic circuitry.
Figure 2:
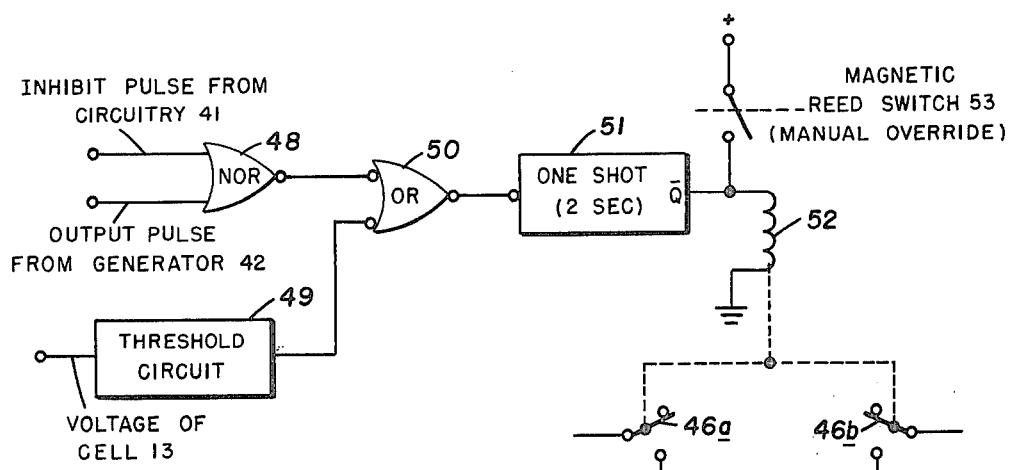
FIG. 2 is a more detailed block diagram of the logic circuitry employed in the embodiment of FIG. 1.

Referring now to FIGS. 1 and 2, a nickel-cadmium cell is illustrated at 13 as the primary power source for the illustrated stimulator and receives recharging energy by means of the input inductive coupler formed by ferrite core 15, pick-up winding 14, diodes 18 and 19 and charge control circuitry generally designated at 40.

In this embodiment of the present invention, it is assumed that the implanted stimulator is a cardiac pacer of the demand inhibited type, such as that disclosed, for example, in U.S. Pat. No. 3,888,260 which issued on my patent application, Ser. No. 464,441, filed Apr. 26, 1974. As a result, the stimulator illustrated in FIG. 1 includes suitable refractory period and demand sensing circuitry 41 which, as is fully described in said patent, (a) monitors to the patient's heart beat by sensing the well-known R-wave and, (b) functions to inhibit the pulse generator 42 if the patient's heart is beating naturally at an acceptable rate, while at the same time insuring that the pacer is not inhibited by a high level T-wave which may appear in the heart's output signal reasonably close in voltage level to the preceding R-wave. The pulse generator 42 might, for example, be designed to have an output pulse rate of 72 pulses per minute, when not inhibited.

In accordance with the present invention, a second power source or battery in the form of a lithium-iodide cell 43, which has a substantial shelf-life because of its very high internal impedance and a very high volumetric energy storage capacity, is connected in parallel with the Ni-Cd cell and is selectively rendered effective when the illustrated control logic 44 senses that the output voltage level from the Ni-Cd cell has dropped below an acceptable level, e.g., 1.0 volt. By way of example, the Ni-Cd cell would typically have a shelf-life (i.e., retains its capacity) of between one and two years and an apparent unlimited operating life if it is recharged. The Li-I cell, on the other hand, typically has a shelf-life in excess of 10 years and likely more than thirty years. Thus and as was noted, the Li-I cell is intended as a stand-by power source in the event of faulty operation of the rechargeable cell. Accordingly, reference herein to the stand-by cell as having a substantial shelf-life is intended to mean that the stand-by cell will be available to power the implanted stimulator unit, if necessary, at any time during some predetermined interval after implant such as, for example, a period in excess of 10 years where a Li-I cell is employed as stand-by. A back-up pulse generator 45 is also provided in the proposed cardiac pacer or stimulator and, while being of the same general configuration as the pulse generator 42, might be designed to operate at a lower pulsing rate, such as fifty pulses per minute versus seventy-two pulses per minute for the circuit 42.

When the control logic 44 senses that the voltage level of the Ni-Cd cell has dropped below 1.0 volt, the illustrated switches 46a and 46b are actuated from their illustrated positions to the lower-most positions wherein (a) the lithium-iodide cell 43 is connected to supply operating voltage to the pulse generator 45 and (b) the output of the pulse generator 45, rather than the output of pulse generator 42, is connected to apply its output pulses to the patient's heart, via the output transformer 11 and leads 12. As will be described in more detail shortly, when considering FIG. 2, the logic circuitry 44 is also designed to actuate the switches 46a and 46b to their lower positions, to thereby render effective the stand-by power source 43 and pulse generator 45, when the pulse generator 42 is not generating output pulses properly at a time when it is not being inhibited by reason of a detected R-wave. As is also shown in FIG. 1, a suitable manual override control 47 can, if desired, be employed to manually actuate the switches 46a and 46b in order to select between the preferred and stand-by batteries and pulse generators.

FIG. 2 of the drawings illustrates in some detail one manner of implementing the control logic 44. More specifically, an NOR logic circuit 48 monitors the inhibit pulse output and pacer output pulse (artifact) from circuits 41 and 42 respectively and its output line remains low or at ground so long as either pulse input is received. By way of example, the inhibit pulse from circuitry 41 might be taken or monitored at the collector of transistor stage 81 in the pulse inhibitor portion of the demand inhibited pacer circuit shown in FIG. 1b of U.S. Pat. No. 3,888,260; whereas, the pacer output pulse could be taken from the collector of transistor stage 41, e.g., on line 80, at the output of the pulse generator portion shown in FIG. 1a of U.S. Pat. No. 3,888,260.

The control logic of FIG. 2 further includes: a threshold circuit 49 which continuously compares the voltage of Ni-Cd cell 13 against a predetermined level such as 1.0 volt; OR gate 50 which is connected to the outputs of NOR gate 48 and threshold detector 49; and, a suitable one shot circuit 51. The trigger input of the one shot 51 is connected to the output of the OR gate 50 such that the one shot 51 is continuously retriggered ($\overline{Q}$ output low) by the pulses at OR gate 50 so long as the threshold detector's output remains low and there are pulses input to NOR gate 48; i.e., the NOR gate 48 is detecting that the pulse generator 42 is either being inhibited by circuit 41 (see FIG. 1) or is generating an output stimulation pulse, and the threshold detector 49 is detecting that the voltage of cell 13 is above the desired 1.0 volt level. The one shot 51 is designed, in the illustrated embodiment, so that its $\overline{Q}$ output goes high (B+) 2 seconds after either the pulse generator 42 is not producing an output pulse at a time when it is not being inhibited by circuitry 41 or if cell 13 voltage is too low. Connected to the $\overline{Q}$ output of the one shot 51 is a relay winding 52 which, when energized, actuates the illustrated switching contacts 46a and 46b to their lower-most position, wherein the stand-by battery 43 and stand-by pulse generator 45 are rendered effective (see FIG. 5). As noted earlier, a manual override control 47 is also contemplated in FIG. 1 so as to permit the operability of the stand-by systems to be checked from time to time; for example, by the magnetic reed switch 53 in FIG. 2 which can be closed by an external magnetic field, as desired.

Figure 3:
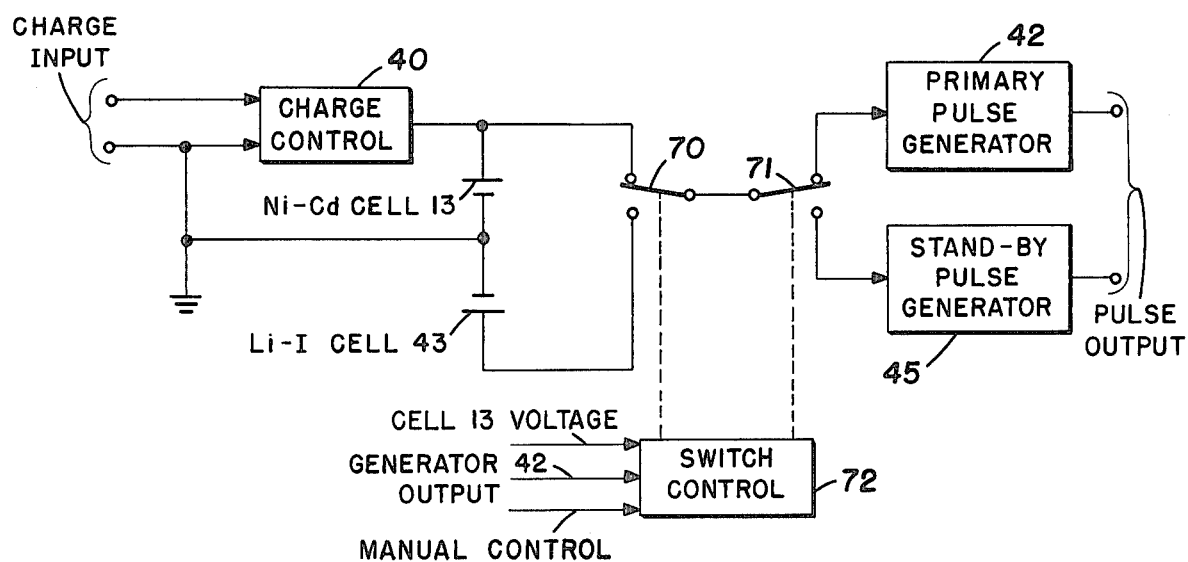
FIG. 3 is a circuit diagram of a further embodiment of the present invention comprising a rechargeable battery which normally supplies operating energy to implanted pulse generating circuitry and a stand-by, long shelf-life battery which can be selectively connected to power the pulse generating circuitry; the pulse generating circuitry also including primary and stand-by pulse generators.

FIG. 3 of the drawings illustrates a still further embodiment of the proposed implanted tissue stimulator. Here again, a Li-I cell 43 is utilized as a stand-by cell for the rechargeable Ni-Cd cell 13, and primary and stand-by pulse generators 41 and 45 respectively are also provided. A pair of switches 70 and 71 interconnect the cells 13, 43 and the pulse generators 42, 45 and are controlled by switch control 72 so that either cell can be connected to furnish operating energy to either pulse generator. By way of example, switch control unit 72, might select the Li-I cell 43, rather than the Ni-Cd cell 13, to power the primary pulse generator 42 if the voltage of the Ni-Cd cell 13 drops below a preselected level, as previously discussed, or in response to a manual control, e.g., override 47 in FIG. 1. Additionally, the switch 71, if desired, can be used to select which of the primary or stand-by pulse generators 42, 45 is connected to the battery (cell 13 or 43); e.g., switch control 72 will operate switch 71 to activate the stand-by generator 45 if the primary generator 42 is malfunctioning, as described above, and/or in response to an external command.

Different embodiments of the present invention have been described hereinabove and it should be understood at this time that various other modifications, adaptations and alterations are possible in light of the above teachings. Therefore, it is contemplated that the invention may be practiced otherwise than as specifically described and still come within the scope of the appended claims.

What is claimed is:

1. An implantable stimulator for applying electrical stimulation to body tissue of a patient comprising,
    means constituting a source of operating energy,
    generator means operably connected to receive operating energy from said source means for generating said electrical stimulation,
    said generator means including a circuit means forming a first primary generator of electrical stimulation and a circuit means forming a second stand-by generator of back-up electrical stimulation,
    circuit means operably connected to said first primary and second stand-by generators for applying said electrical stimulation, and
    control means responsive to the output of said first primary generator for selectively rendering said second stand-by generator effective to apply said back-up stimulation if said first primary is not properly generating said electrical stimulation.--

2. The implantable stimulator specified in claim 1
    wherein said source means includes first and second batteries,
    wherein said first battery is connected to supply operating energy to first primary generator, and
    wherein said second stand-by generator is adapted to receive operating energy from said second battery.--

3. The implantable stimulator specified in claim 2 wherein said control means also responds to the voltage output from said first battery for selevtively rendering said second stand-by generator effective to generate said back-up stimulation if the voltage output from said first battery decreases below a predetermined level.--

4. The implantable stimulator specified in claim 2 including means for recharging said first battery from an external source, wherein said second battery is a stand-by battery having a substantial shelf-life, and wherein said control means includes a switch means for connecting said second battery to said second stand-by generator.--

5. The implantable stimulator specified in claim 1 wherein said first primary generator includes means to inhibit the generation of said electrical stimulation and wherein said control means includes means for checking to determine if said first primary generator is inhibited prior to rendering effective said second stand-by generator.--

6. The implantable stimulator specified in claim 1 wherein said back-up electrical stimulation has a characteristic distinctive from the electrical stimulation generated by said first primary generator.--

7. The implantable stimulator specified in claim 1, wherein said source means includes a first rechargeable battery and a second battery having a substantial shelf-life, and
wherein said control means further includes a first switch means for selectively connecting either of said first and second batteries to apply operating energy to said first primary generator.--

8. The implanted stimulator specified in claim 7 wherein said control means further includes a second switch means for selectively connecting either of said first and second batteries to apply operating energy to either of said first and second generators.--

* * * * *